United States Patent [19]

Su et al.

[11] Patent Number: 4,921,969
[45] Date of Patent: May 1, 1990

[54] METHOD FOR THE PREPARATION OF IMIDAZOLES

[75] Inventors: Wei-Yang Su; George P. Speranza, both of Austin, Tex.

[73] Assignee: Texaco Chemical Co., White Plains, N.Y.

[21] Appl. No.: 284,883

[22] Filed: Dec. 15, 1988

[51] Int. Cl.$^5$ .......................................... C07D 233/58
[52] U.S. Cl. ................................... 548/335; 548/346
[58] Field of Search ................................ 548/335, 346

[56] References Cited

U.S. PATENT DOCUMENTS 2,847,417 8/1958 Erner .................................. 548/335
3,152,998 10/1964 Moss ................................ 544/358 X

FOREIGN PATENT DOCUMENTS 3009605 10/1981 Fed. Rep. of Germany .

OTHER PUBLICATIONS

*Chemical Abstracts,* 70:28867g (1969) [N. Sawa, *Nippon Kagaku Zasshi* 1968, 89(9), 868–72].

Primary Examiner—Richard A. Schwartz
Attorney, Agent, or Firm—Jack H. Park; Kenneth R. Priem; Cynthia L. Kendrick

[57] ABSTRACT

This invention discloses an improved method for preparation of imidazoles without isolation of the imidazoline intermediate which comprises reacting a diamine with carboxylic acid and heating the mixture at a temperature of 140°–300° C. at a pressure of subatmospheric to about 10 atm to form an amide, passing the amide over a nickel-containing catalyst at a temperature of 180° C. to 250° C. and a pressure of atmospheric to 200 psig and isolating the imidazole.

15 Claims, No Drawings

METHOD FOR THE PREPARATION OF IMIDAZOLES

CROSS-REFERENCE

This application is related to U.S. application Ser. No. 284,884, filed of even date.

FIELD OF THE INVENTION

This invention relates to an improved method for preparation of imidazoles. More particularly, this invention relates to a method for the selective preparation of imidazoles which does not require isolation of an imidazoline intermediate. The method comprises reacting a diamine and organic acid to form aminoethyl amides and passing said amides over a catalyst comprising nickel alone or nickel in combination with specific proportions of one or more transition metals at mild temperatures and atmospheric pressure.

Unexpected advantages are observed by virtue of the fact that very high yields are observed and yet the method eliminates the step requiring isolation of the intermediate imidazoline.

BACKGROUND OF THE INVENTION

Imidazoles and simple imidazole derivatives are being used more often as hardening agents for epoxy resins. They provide long pot life, high heat distortion temperatures, economical performance based on low PHR requirements and are less toxic than amines. They are useful accelerators for anhydride cure and bisphenol-A cure of epoxy resins. The imidazole ring can be utilized in numerous reactions and the derivatives can be used for specialty epoxies. For example, delayed action can be obtained by acylating imidazoles with polychlorinated benzoyl chloride. See U.S. Pat. No. 4,436,892.

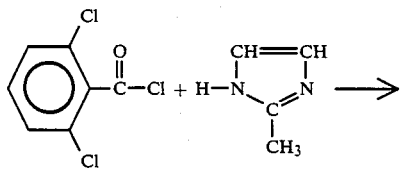

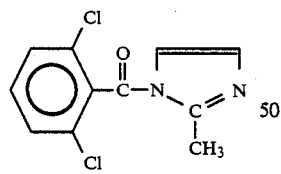

Imidazoles are characterized by their essentially aromatic character, high boiling points, and good stability to oxidizing and reducing agents. They undergo typical aromatic reactions such as nitration, chlorination and diazo coupling. The 2-alkyl and 2-alkenyl imidazoles show a strong detergent and emulsifier action in petroleum oils and they protect metals in contact with such oils.

The long chain 2-alkyl imidazoles are surface active agents and the corresponding quaternary compounds show typical germicidal properties of cationic surfactants. Some other uses include fabric softeners (*Europa Chemie* Apr. 30, 1983, p. 195), antifungal agents (*World Pharmaceutical News,* Apr. 20, 1981, p. 15), photosensitive product reagents for the preparation of urethane resins, catalysts for the preparation of polyesters and polyurethanes, plastic additives, anticonvulsant drugs, and antimicrobial agents. Certain imidazoles are effective in the control of anthrenus flavipies, an insect pest of wool.

Early synthesis of imidazoles involved the reaction of 1,2-dicarbonyl compounds with ammonia and aldehydes to produce low yields according to the equation:

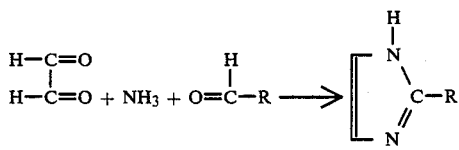

The yields could be increased if the reaction was carried out in organic acid with ammonium acetate. Radziszewski, R. Ber, 15, 2706 (1882).

Imidazole oxalate, fumarate, adipate, phthalate and 4-methylimidazole, 4,5-dimethylimidazole and 2-isopropylimidazole have been made from the $\alpha,\beta$-dicarbonyl compounds, as demonstrated is U.S. Pat. No. 3,715,365.

Werdenhazen, R., and Rienacker, H., Ber. 72, 57 (1939) demonstrated the production of imidazoles from $\alpha$-hydroxyketones under the influence of ammoniacal cupric acetate and aldehydes represented by the following:

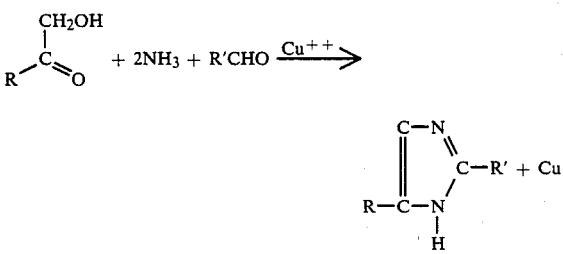

In "New Methods of Preparative Organic Chemistry", Vol. 3, p. 241, Academic Press. N.Y., 1964, H. Budereck, et al. describe another method involving formamide synthesis according to the equation:

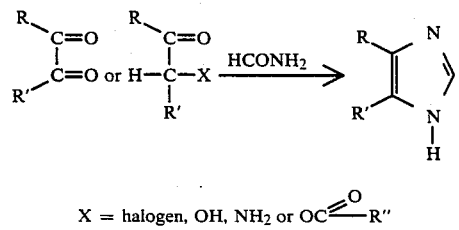

$X$ = halogen, OH, $NH_2$ or $OC\overset{O}{\diagup\!\!\!\diagup}R''$

Some 2-methylimidazoles have been prepared using acetamides; however, yields were reduced when amides other than formamide were used.

One of the more attractive methods for producing imidazoles is discussed in U.S. Pat. No. 2,891,966. This involved the reaction of a 1,2-diamine with carboxylic acids. For instance, ethylenediamine was admixed with a slight excess of acetic acid, permitting an exothermic rise which dissolved the reagents. The homogeneous solution was cooled to about 100° C., then charged through a continuous reactor equipped with a preheater section (a reactor section filled with platinum). Then the reactor was heated to 430° C. and hydrogen added. The vaporous reaction effluent was condensed to obtain crystalline 2-methyl imidazole.

A French patent describes the purification of 2-methyl imidazole by codistilling it with 1- or 2-methylnaphthalene and then washing with pentane or toluene. See French P. 1,362,689 (1964).

In other work, the diamine is converted to 2-alkyl imidazoline, and then dehydrogenated to the corresponding imidazole compound by dehydrogenation over a nickel catalyst. For example see U.S. Pat. No. 2,399,601 and U.S. Pat. No. 2,404,299 on the preparation of imidazoles by heating imidazolines with Raney nickel catalysts. The reactions were carried out at 225°–235° C. The yields were not reported in some cases or varied widely. In these patents the intermediate imidazoline had to be isolated.

H. A. Green, of Air Products has demonstrated that 1,2-diamines can be reacted with aldehydes and then heated over a platinum-alumina catalyst at 370° C. to give imidazoles. In the case of ethylenediamine and propionaldehyde a 56% yield of 2-ethyl imidazole was obtained. See U.S. Pat. No. 3,037,028, May 29, 1962.

In U.S. Pat. No. 3,037,028, using another vapor phase reaction, Green demonstrated that imidazole could be obtained from ethylenediamine and formamide using a large volume of hydrogen. See also U.S. Pat. No. 3,255,200. The catalyst used was platinum-on-alumina and alumina or cobalt molybdate were shown to be ineffective. Treating ethylenediamine with methyl formate at 25°–30° C. gave 98.5% diformyl derivative.

In Ger. Offen. DE 3,009,605, diformyl derivative was passed with nitrogen over 6:14 NiO:MoO$_3$ at 400° C. to give 65.7% imidazole with 99.3% conversion. The yield remained constant after 250 hours use of the catalyst.

Imidazolines can be dehydrogenated to imidazoles at 250°–500° C. over MoO$_3$ and NiO and/or CoO and Al$_2$O$_3$, SiO$_2$ and/or alkaline silicate catalysts. See DE 3,009,631. This reaction has been used to make a variety of 2-alkylimidazoles substituted with long chain fatty acids. As noted, the minimum temperature requirement is 250° C.

Another route to imidazoles involved the reaction of a nitrile with a diamine over a copper salt to give imidazolines which were then dehydrogenated over an aluminum-zinc oxide catalyst to give imidazoles, involving two distinct steps. See DE 3,236,598-A to BASF.

In U.S. Pat. No. 4,409,389, hexamethylene-tetramine was reacted with formamide at 140° C. to give a bis-formamide. The bis-formamide with dicarbonyl compounds and 2 moles of mineral acid yielded imidazole acid salts.

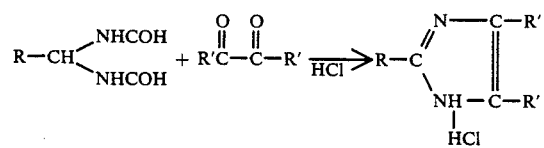

In Ger. Offen. 1,952,991, imidazole was made in 53% yield by passing a solution of ethylenediamine and formic acid over a Cd-Cu chromite catalyst at 480° C. This method required quite high temperatures and the yield was very moderate.

Imidazolines have been dehydrogenated with sulfur and manganese dioxide.

In copending application Ser. No. 284,884 there is described the preparation of imidazoles by the dehydrogenation of imidazolines over a nickel catalyst in combination with chromium and/or copper.

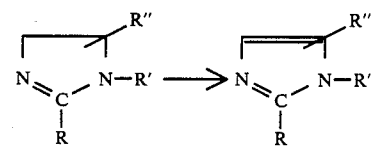

It is noted that most methods for producing imidazoles which are found in the art require higher temperatures and the yields reported are not as high as would be desirable. Some require catalysts which are expensive and would be a deterrent to commercial use. Most procedures require several steps, including isolation of an intermediate imidazoline and subsequent dehydrogenation to the imidazole.

It would be a substantial advance in the art if high yields of imidazoles could be prepared from readily available reactants such as carboxylic acids and diamines without the need to isolate the imidazoline intermediate. Such a process would be extremely attractive commercially.

SUMMARY OF THE INVENTION

In accordance with the foregoing, the present invention provides a method of preparing imidazoles by reacting a diamine with an organic acid, heating the reactants to form an amide, reacting the mixture over a catalyst comprising nickel alone or in combination with one or more transition metals, preferably copper and/or chromium, at a temperature of 140° C. to 250° C. and a pressure of subatmospheric to 10 atm and isolating the imidazole. The yields are almost quantitative when N-alkylethylenediamines are used and this method eliminates the isolation of the intermediate imidazoline.

The products of this invention include:
1-3'-pentyl-2-methylimidazole;
1-4'-methyl-2'-pentyl-2-methylimidazole
1-isopropyl-2-methylimidazole
1-isopropyl-2-undecylimidazole
1-isopropyl-2-tridecylimidazole
which can be used, among other things, as hardening agents for epoxy resins.

DETAILED DESCRIPTION OF THE INVENTION

This invention describes a selective process for the preparation of imidazoles. According to the invention, a diamine and an organic acid are reacted and heated to a temperature of 140° C. to 300° C. to form an amide and said amide is passed over a catalyst comprising nickel alone or in combination with copper and/or chromium, and thereafter the imidazole is isolated. The imidazole products can be derived in high yield at mild conditions without isolation of the intermediate and minimal formation of by-products.

This can be represented by the following equation:

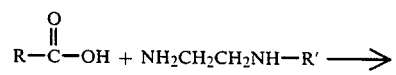

-continued

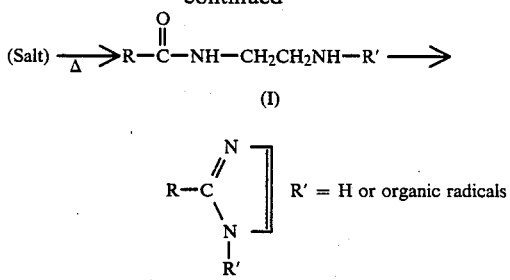

As stated, the reactants useful in the invention are diamines and organic acids. The diamines which will work include alkylene diamines. The preferred diamines are ethylenediamines of the formula

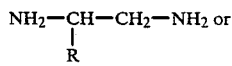

N-alkylethylenediamines of the formula

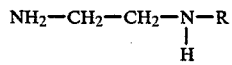

wherein R is alkyl or hydrogen or aromatic. Examples include N-methyl, N-isopropyl, N-isobutyl, N-methylisobutyl ethylenediamines and 1,2-propylenediamine derivatives.

Suitable organic acids are primarily aliphatic carboxylic acids having 1 to 18 carbon atoms. Examples include propionic, isobutyric, acetic acid, lauric acid and myristic acid. Aromatic carboxylic acids may also be used.

The organic acid and diamine are simply heated to form an amide which is subsequently passed over the catalyst at about 200° C. to give the imidazoles without the necessity of isolating the intermediate imidazoline.

In other work metal catalysts have been used as dehydrogenation catalysts, in two-step syntheses of imidazoles; however, it has been surprisingly discovered in the instant invention that the imidazoles can be prepared from the aminoethylamide reaction product without the isolation of the imidazoline intermediate. In addition almost quantitative yields are obtained when N-alkyl ethylenediamines are used. Those skilled in the art will recognize how desirable such features are for commercial reasons.

The catalyst comprises nickel combinations with one or more transition metals. Transition metals which can be used in conjunction with the nickel include manganese, iron, zinc, copper and chromium. The preferred catalyst was obtained where the nickel was combined with copper and/or chromium.

The quantity of nickel compound and copper or chromium employed in the catalyst may vary. The reaction proceeds when employing as little as about 50 percent of nickel together with about 0 weight percent of copper and 0% chromium, basis the total weight of the catalyst. The percentage of copper and/or chrome is desirable about 2 to about 30%. From 70 to about 80 wt% of nickel in conjunction with from about 20 to 30 of copper and/or chromium is generally preferable. The preparation of such catalysts is described in U.S. Pat. No. 3,152,998.

Suitable catalyst compositions include 70 to 95 weight percent nickel and from 5 to 30% copper-containing compound; 80 to 99 percent nickel in combination with 1 to 20% chromium; 60 to 80% nickel, 14 to 37% copper and 1 to 5% chromium; 72 to 78% nickel, 20 to 25% copper and 1 to 3% chromium; and 95 to 99.8% nickel and 0.2 to 5% chromium.

The temperature range which can usefully be employed is variable depending upon other experimental factors, including the pressure and the choice of particular species of catalyst among other things. The range of operability is from about 140° C. to 300° C. A narrow range of 180° to 250° is preferred and reflects significantly milder temperatures than previously used in the art for similar reactions.

Pressures of subatmospheric to 10 atm can be used. Substantial yields are realized using atmospheric pressure.

The products are imidazoles having the general structure:

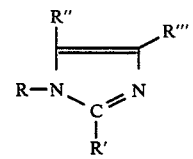

where R is H or an alkyl group containing 1–18 carbon atoms; R' is H, an aromatic or alkyl group containing 1 to 17 carbon atoms; R" is H or an alkyl group containing 1–4 carbon atoms; and R'" is H, or an alkyl group containing 1–4 carbon atoms.

As noted specific products demonstrated in this invention include:
1-3'-pentyl-2-methylimidazole;
1-4'-methyl-2'-pentyl-2-methylimidazole
1-isopropyl-2-methylimidazole
1-isopropyl-2-undecylimidazole
1-isopropyl-2-tridecylimidazole These imidazole and simple imidazole derivatives are being used more as hardening agents for epoxy resins. They provide long pot life, high heat distortion temperatures, economical performance based on low PHR requirements and lower toxicity than amines. They are useful accelerators (catalysts) for anhydride cure and bisphenol-A cure of epoxy resins. The imidazole ring can be utilized in numerous reactions and these derivatives can be used for specialty epoxies.

The process can be conducted in a kettle, tubular reactor or a glass reactor. The catalyst may be initially introduced into the reaction zone batchwise, or it may be continuously or intermittently introduced into such a zone during the course of the synthesis reaction. Operating conditions can be adjusted to optimize the formation of the desired imidazole products. The products are recovered preferably by fractional distillation.

The products have been identified by one or more of the following analytical procedures, viz, gas-liquid chromatograph (glc), infrared (IR), nuclear magnetic resonance (nmr) and mass spectra or a combination of these techniques. Analyses have, for the most part, been by parts in weight; all temperatures are in degrees centigrade and all pressures in pounds per square inch guage (psig). The selectivity means the moles of imidizole produced divided by moles of reactants.

Various embodiments of the process of this invention are illustrated in the following examples which are not to be considered limitative:

EXAMPLE 1

Preparation of 1-3'-Pentyl-2-methylimidazole

A 250-ml three-necked flask equipped with a thermometer, condenser, stirrer, and nitrogen inlet was charged with N-3'-pentylethylenediamine (104 g, 0.8 mol). Acetic acid (48 g, 0.8 mol) was added dropwise over a 10 minute period. After finishing the acid addition, the mixture was heated to 130°-140° C. for two hours. The reaction mixture was cooled to room temperature. A Dean-Stark trap was added and Harshaw Ni-2715 catalyst was also added. The mixture was heated to 200° C. for five hours. The resulting reaction mixture was filtered and about 118 g of crude product was obtained. GLC analysis showed that the crude product contained 99% of 1-3'-pentyl-2-methylimidazole. The product was fractionally distilled under reduced pressure (92° C. at 0.5 mm Hg) to give a clear, colorless liquid in about 91% yield.

EXAMPLE 2

Preparation of 1-4'-methyl-2'-pentyl-2-methyl-imidazole

The procedure of Example 1 was followed except that 100.8 g (0.7 mol) of N-4'-methyl-2'-pentylethylenediamine and 42 g (0.7 mol) of acetic acid were used. GLC analysis showed that the crude product contained 99% of 1-4'-methyl-2'-pentyl-2-methylimidazole. The product was fractionally distilled under reduced pressure (85° C. at 0.35 mm Hg) to give a clear, colorless liquid in about 89% yield.

EXAMPLE 3

Preparation of 1-Isopropyl-2-methylimidazole

The procedure of Example 1 was followed except that 33.1 g (0.32 mol) of N-isopropylethylenediamine, 19.4 g (0.32 mole) of acetic acid and 5.9 g of Harshaw Ni-2715 catalyst were used. About 37.6 g of crude product was recovered. GLC analysis showed that the crude product contained 98% of 1-isopropyl-2-methylimidazole.

EXAMPLE 4

Preparation of 1-Isopropyl-2-undecylimidazole

A 100-ml three-necked flask equipped with a thermometer, Dean-Stark trap, stirrer, and nitrogen inlet was charged with 26.0 g of N-2'-isopropylaminoethyldodecanamide (prepared from lauric acid and N-isopropylethylenediamine) and 3.7 g of Harshaw Ni-2715 catalyst. The mixture was heated to 200° C. for five hours. The resulting reaction mixture was filtered and about 20.3 g of light-green liquid product was obtained. The IR spectrum of this product indicates it to be that of 1-isopropyl-2-undecylimidazole.

EXAMPLE 5

Preparation of 1-Isopropyl-2-tridecylimidazole

The procedure of Example 4 was followed except that 32.2 g of N-2'-isopropylaminoethyltetradecanamide (prepared from myristic acid and N-isopropylethylenediamine) and 4.4 g of Harshaw Ni-2715 catalyst were used. About 25.5 g of light green liquid product was obtained. The IR spectrum of this product indicated it to be 1-isopropyl-2-tridecylimidazole.

What is claimed is:

1. An improved method for preparation of imidazoles not requiring isolation of the imidazoline intermediate which comprises:

reacting a diamine with a compound from the group consisting of nitriles and organic acids, heating the mixture at a temperature of 140°-300° C. at a pressure of subatmospheric to about 10 atm, forming an amide and passing the amide over a nickel-containing catalyst selected from the group consisting of nickel-copper, nickel-chromium and nickel-copper-chromium and isolating the imidazole.

2. The method of claim 1 wherein the diamine is an alkylenediamine.

3. The method of claim 2 wherein the alkylenediamine is from the group consisting of 1,2-propylenediamine, 1,2-butylenediamine, 2,3-butylenediamine and ethylenediamine.

4. The method of claim 3 wherein the ethylenediamine has a formula selected from the group consisting of

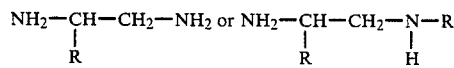

where R is selected from the group consisting of alkyl, hydrogen or an aromatic.

5. The method of claim 1 wherein the organic acids are aliphatic or aromatic carboxylic acids with from 1 to 18 carbon atoms.

6. The method of claim 1 wherein the amide is heated at a temperature from 180° C. to 250° C.

7. The method of claim 1 wherein the catalyst comprises nickel in combination with copper.

8. The method of claim 1 wherein the catalyst comprises nickel in combination with chromium.

9. The method of claim 7 wherein the catalyst comprises nickel in combination with mixed copper and chromium.

10. The method of claim 1 wherein the catalyst consists of from 70 to 98 weight percent nickel in combination with from 2 to 30 weight percent cocatalyst from the group consisting of copper, chromium, or mixed copper-chromium.

11. The method of claim 7 wherein the catalyst comprises 70 to 95 weight percent nickel and from 5 to 30% copper-containing compound.

12. The method of claim 8 wherein the catalyst comprises 80 to 99 percent nickel in combination with 1 to 20% chromium.

13. The method of claim 9 wherein the catalyst comprises 60 to 80% nickel, 14 to 37% copper and 1 to 5% chromium.

14. The method of claim 9 wherein the catalyst comprises 72 to 78% nickel, 20 to 25% copper and 1 to 3% chromium.

15. The method of claim 8 wherein the catalyst comprises 95 to 99.8% nickel and 0.2 to 5% chromium.

* * * * *